United States Patent
Alkemper et al.

(10) Patent No.: US 6,362,251 B1
(45) Date of Patent: Mar. 26, 2002

(54) DENTAL MATERIAL COMPRISING POROUS GLASS CERAMICS, POROUS GLASS CERAMICS, PROCESSES AND USE

(75) Inventors: Jochen Alkemper, Viernheim; Harald Rentsch, Hanau; Klaus Dermann, Bad Nauheim; Hans-Joachim Ritzhaupt-Kleissl, Walldorf; Jurgen Hausselt, Germersheim; Philipp Albert, Hanau; Corinna Gall, Schluchtern, all of (DE)

(73) Assignee: Degussa-Huls Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/409,560

(22) Filed: Sep. 30, 1999

(30) Foreign Application Priority Data

Oct. 9, 1998 (DE) .......................... 198 46 556

(51) Int. Cl.⁷ ............................. A61K 6/08; C08K 3/32
(52) U.S. Cl. .................. 523/116; 523/209; 523/217; 106/35; 433/228.1; 524/492; 524/493; 524/701; 524/780; 524/783; 524/784; 524/785; 524/786; 524/847
(58) Field of Search ................................. 523/109, 116, 523/117, 118, 209, 217; 106/35; 433/228.1; 524/492, 493, 701, 780, 783, 784, 785, 786, 847

(56) References Cited

U.S. PATENT DOCUMENTS

| | | | | |
|---|---|---|---|---|
| 4,381,918 A | * | 5/1983 | Ehrnford | 523/116 |
| 4,707,504 A | * | 11/1987 | Walkowiak et al. | 523/116 |
| 4,925,660 A | | 5/1990 | Atsuta et al. | 522/24 |
| 4,952,530 A | * | 8/1990 | Brosnan et al. | 433/228.1 |
| 5,350,782 A | | 9/1994 | Sasaki et al. | 523/116 |
| 5,426,082 A | | 6/1995 | Marsden | 502/235 |
| 5,556,896 A | | 9/1996 | Byerley et al. | 523/116 |
| 5,733,949 A | * | 3/1998 | Imazato et al. | 523/109 |
| 5,750,590 A | | 5/1998 | Schaefer et al. | 523/115 |
| 5,852,096 A | * | 12/1998 | Heindl et al. | 523/116 |
| 5,877,232 A | | 3/1999 | Storch et al. | 523/116 |
| 5,952,399 A | | 9/1999 | Rentsch | 523/116 |
| 6,031,015 A | | 2/2000 | Ritter et al. | 522/77 |
| 6,124,491 A | | 9/2000 | Wolter et al. | 556/438 |
| 6,245,828 B1 | | 6/2001 | Weinmann et al. | 523/116 |

FOREIGN PATENT DOCUMENTS

| | | |
|---|---|---|
| DE | 41 33 494 | 4/1993 |
| DE | 44 16 857 | 6/1995 |
| DE | 195 06 222 | 8/1996 |
| DE | 196 15 763 | 10/1997 |
| DE | 196 48 283 | 5/1998 |
| EP | 0 048 681 | 3/1982 |
| EP | 0 04 8681 | 3/1982 |
| EP | 0 43 4334 | 6/1991 |
| EP | 0 530 926 | 3/1993 |
| EP | 0 754 675 | 1/1997 |
| EP | 0 83 2636 | 4/1998 |
| EP | 0 83 9511 | 5/1998 |

OTHER PUBLICATIONS

Abstract of LR above.
Abstract of NR above.
Abstract of KR above.
Abstract of LR above.
Abstract of MR above.
Abstract of NR above.
Abstract of OR above.
Abstract of ZR above.
Abstract of QR above.
Abstract of RR above.

* cited by examiner

*Primary Examiner*—Peter Szekely
(74) *Attorney, Agent, or Firm*—Pillsbury Winthrop LLP

(57) ABSTRACT

Dental material based on polymerizable (for example ethylenically unsaturated) monomers, epoxides, ormocers, liquid crystal monomers, oxethanes, spiro-orthoesters or spiro-carbonates as binders, a catalyst for cold, hot and/or photo-polymerization, and fillers, and a process for its preparation. Porous glass ceramics, a process for their preparation and uses thereof are also described. Dental materials according to the invention are suitable as alternative materials to the use of amalgam fillings.

9 Claims, No Drawings

DENTAL MATERIAL COMPRISING POROUS GLASS CERAMICS, POROUS GLASS CERAMICS, PROCESSES AND USE

This application claims priority from German Application No. 198 46 556.4, filed on Oct. 9, 1998, the subject matter of which is hereby incorporated herein by reference.

BACKGROUND OF THE INVENTION

1. Field of the Invention

The present invention relates to a dental material and a process for the preparation thereof. The invention also relates to porous glass ceramics, a process for their preparation and their use.

The invention particularly relates to dental materials based on polymerizable, for example ethylenically unsaturated monomers, epoxides, ormocers, liquid crystal monomers, oxethanes, spiro-orthoesters or -carbonates as binders, a catalyst for cold, hot and/or photo-polymerization and, based on the dental material, 20–70 wt. % of an inorganic filler (A) and, based on the dental material, 0–60 wt. % of other fillers (B) and 0–2 wt. % of other conventional additives.

2. Background Information

Because of the possible health risks of mercury-containing materials (amalgams) in the field of tooth restoration, new mercury-free formulations are increasingly being sought for this intended use.

Porous glass ceramics which are used for the preparation of special catalysts are known from U.S. Pat. No. 5,426,082. The ceramics mentioned there are said to have a minimum pore volume of >2000 mm$^3$/g. These high pore volumes make these substances unsuitable as filling materials in dental materials, since they result in low strength of the fillings.

The inorganic porous particles with filler contents described in EP 48 681 are fillers consisting of amorphous glasses. However, the dental materials mentioned here have the disadvantage that, because of their structure and size, the particles of the filler can enter the lungs thereby giving rise to the risk of a disease comparable to asbestosis.

EP-A 0 530 926 discloses dental compositions of a polymerizable monomer and an inorganic filler which comprises, in a proportion of 20 to 80 wt. %, spherical inorganic oxide particles with an average particle size of between 1.0 and 5.0 μm and, in a proportion of 80–20 wt. %, spherical inorganic oxide particles with a particle size in the range of at least 0.05 μm and less than 1.0 μm, at least 5 wt. % of the last component being in the range from 0.05 to 0.2 μm. The inorganic particles are exclusively spherical particles of inorganic oxides of silicon, zirconium, aluminium and titanium, or mixed oxides of metals of main groups I–IV of the periodic table with silicon. The spherical particles are prepared, for example, by hydrolytic polymerization of alkoxysilanes and can also be surface-treated for example with γ-methacryloxypropyltrimethoxysilane.

DE 196 15 763 describes amorphous silicon dioxide glasses charged with monomers in dental composites.

The plastics-based tooth restoration materials which can be prepared from fillers in accordance with these last documents are inferior to amalgams in several respects:

- the filling materials are not sufficiently abrasion-resistant to be used in the chewing region of teeth
- the non-porous materials usually polymerized into the polymer mixtures, such as, for example, glass particles, must be coated with special coupling reagents and are often susceptible to hydrolytic cleavage reactions between the polymer material and filler. This reduces the abrasion resistance by the fillers breaking out.
- filling materials which are based on porous amorphous glasses have the disadvantage that the filling materials are not opaque to X-rays and have a refractive index which differs from the surrounding polymer matrix by more than 0.02, which results in cloudy dental materials of low transparency which are difficult to cure by means of light in one step and therefore have to be polymerized into the cavity in layers in an expensive manner.

SUMMARY OF THE INVENTION

The object of the present invention is therefore to provide dental materials which do not have the disadvantages of the materials of the prior art, and in particular have an increased strength and improved abrasion resistance with a comparably good polymerization shrinkage. Furthermore, the detachment of the polymer matrix from the inorganic filler caused by hydrolytic cleavage should be suppressed. The dental material should moreover be opaque to X-rays, if desired, and transparent such that the dental material can be introduced into the cavity of the tooth and cured by means of light in one working step.

It is another object of the invention to provide certain glass ceramics which are suitable as porous fillers for use in dental materials according to the invention.

This object, where it relates to a dental material, is achieved by a dental material comprising an inorganic filler (A), a porous glass ceramic having micro- and/or mesopores charged with polymerizable, ethylenically unsaturated monomers, epoxides, ormocers, liquid crystal monomers, oxethanes, spiro-orthoesters or -carbonates or with the polymerized form thereof. In preferred embodiments, filler (A) has a pore size greater than 10 nm and less than 100 nm, a particle size between 10 and 30 μm, and/or a pore volume greater than 500 mm$^3$/g and less than 1500 mm$^3$/g. Preferably, filler (A) comprises oxides of metals of main groups 1 to 4 and oxides of metals of the sub-groups, which are preferably present in filler (A) individually or as a mixture in an amount of between 1 and 50 wt. %

The invention also provides a process for the preparation of the dental material. In preferred embodiments of the process, filler (A) may charged with gaseous polymerizable, ethylenically unsaturated monomers or with liquid polymerizable, ethylenically unsaturated monomers before formulation of the dental material. The polymerizable, ethylenically unsaturated monomers present in filler (A) before formulation of the dental material may also be converted into their polymerized form. Filler (A) may be additionally charged with bactericidal agents, and the surface of filler (A) and/or (B) may be chemically modified.

The invention also provides a porous glass ceramic charged with polymerizable, ethylenically unsaturated monomers or with the polymerized form thereof. In preferred embodiments, the pore size of the glass ceramic is greater than 1 nm and less than 1000 nm, the particle size is between 10 and 30 μm, and/or the pore volume is greater than 150 mm$^3$/g and less than 1500 mm$^3$/g. The glass ceramic may comprise oxides of metals of main groups 1 to 4 and oxides of metals of the sub-groups. The oxides may be present, for example, in an amount between 1 and 50 wt. %.

The invention also provides a process for the preparation of the porous glass ceramics of the invention. In one embodiment, the glass ceramic is prepared by mixing an aqueous $SiO_2$ sol and one or more sols of oxides of metals of main groups 1 to 4 and of oxides of metals of the sub-groups. An aqueous solution of a salt may be added to the total sol. Furthermore, 0–10 wt. % (based on the sol mixture) of organic solvents may be added to the sol mixture. In one embodiment, the sol mixture may be spray-dried and optionally calcined at >800° C. and <1300° C.

The porous glass ceramics according to the invention may be charged with polymerizable, ethylenically unsaturated compounds and used in the dental materials according to the invention.

By providing a dental material based on polymerizable, for example ethylenically unsaturated monomers, epoxides, ormocers, liquid crystal monomers, oxethanes, spiro-orthoesters or -carbonates as binders, a catalyst for cold, hot and/or photo-polymerization and, based on the dental material, 20–70 wt. % of an inorganic filler (A) and, based on the dental material, 0–60 wt. % of other fillers (B) and 0–2 wt. % of other conventional additives, where the inorganic filler (A) is a porous glass ceramic in which the micro- and/or mesopores are charged with polymerizable, ethylenically unsaturated monomers, epoxides, ormocers, liquid crystal monomers, oxethanes, spiro-orthoesters or -carbonates or with the polymerized form thereof, a dental material which is optionally opaque to X-rays, has a transparency which can be adjusted to the particular conditions in a controlled manner and, with a good polymerization shrinkage comparable to the materials of the prior art, has an improved strength with a simultaneously improved abrasion resistance results.

The pore size (pore diameter/width) of filler (A) is consequently responsible for how well the monomers can enter filler (A). A dental material in which the glass ceramic filler (A) has a pore size of greater than 1 nm and less than 1000 nm is preferred. The pore size of filler (A) is particularly preferably between 10 nm and 100 nm.

As a result, the pores can be filled completely with the polymerizable monomers, and at the same time a high transparency can be achieved (no interference effects) due to the small dimensions of the pores compared with the wavelength of visible light.

According to the invention, the particle size of filler (A) can be between 1 and 50 $\mu$m, particularly preferably between 10 and 30 $\mu$m.

The pore volume of filler (A) is an essential characteristic for the preparation of the dental material. The pore volume must not be too large, since otherwise the internal cohesion of the glass ceramic decreases. If it is too small, the adhesion between the filler and matrix decreases, so that the surface of the dental material is very rough and the wear increases. For these reasons, the pore volume of filler (A) should be greater than 200 $mm^3/g$ and less than 2000 $mm^3/g$. A size between 500 $mm^3/g$ and 1500 $mm^3/g$ is preferred.

The glass ceramic filler (A) is built up from an amorphous glass content in which crystalline regions, which can comprise oxides of metals of main group 1 to 4 and oxides of metals of the sub-groups, are embedded.

The content of oxides, which can occur in filler (A) individually or as a mixture, can be between 1 and 50 wt. %, based on filler (A).

In the polymerized state, the ratio of the parts by wt. of polymer to filler (A) to fillers (B) of the dental fillings according to the invention can be in the ratio range of 10–80 to 20–70 to 1–30, preferably 30–50 to 30–60 to 5–20 (100 in total).

Bactericidal agents can thus be implemented in filler (A). Hesperedin, naringenin, quercetin, anisic acid, acetyl coumarin, sitosterol, caryophyllene and caryophyllene oxide are regarded as bactericidal agents. These compounds can be incorporated into the pores of filler (A) by the processes described in U.S. Pat. No. 4,925,660.

The internal and/or external surface of the micro- and/or mesoporous glass ceramic fillers (A) and the external surface of filler (B) can preferably optionally be chemically modified with the surface materials with which the person skilled in the art is familiar before use in the dental material. This serves inter alia to a) increase the mechanical stability and hydrophobicity and
b) further improve the coupling of the inorganic filler to the organic matrix.

In a particular embodiment, filler (A and/or B) is subsequently coated with silanes of the general formula RSi(OX)$_3$, wherein R is an alkyl group having 1 to 18 C atoms and X is an alkyl group having 1 or 2 C atoms, and/or metal oxides. To increase the stability and hydrophobicity, trimethylchlorosilane is used in particular, as described in Koyano, K. A.; Tatsumi, T.; Tanaka, Y.; Nakata, S. J. Phys. Chem. B 1997, 101, p. 9436 and Zhao, X. S.; Lu, G. Q., J. Phys. Chem. B 1998, 102, p. 1156. If a silane is used for the subsequent coating, it is expedient if this is used in an amount of about 0.02 to 2 per cent by weight of the silane, calculated as $SiO_2$, based on the weight of filler (A) and (B).

For the dental composition according to the invention it is advantageous that the colour, transparency and opacity to X-rays can already be adjusted solely by the composition of filler (A). However, other metal oxides can optionally also be employed for the subsequent coating, this preferably taking place in an amount of 1 to 100 per cent by weight, preferably 10 per cent by weight, based on the metal oxide content of fillers (A) and (B) which have not been after-coated.

Particularly advantageous agents for the subsequent coating include, inter alia, $(CH_3)_3SiCl$, methyltriethoxysilane, ethyltriethoxysilane, octyltriethoxysilane, octadecyltriethoxysilane, mono- or polyfluoroalkylethoxysilane or also silanes with functionalized organo groups, which allow further later modification by covalent bonding in a known manner. In the latter case, those organotrialkoxysilanes which contain such functional groups with which covalent bonding into the polymer material can be achieved are preferred in respect of the use according to the invention of the particles as fillers in polymeric or polymerizable systems. Examples of these are trimethoxyvinylsilane, $H_2C=C(CH_3)CO_2(CH_2)_3Si(OCH_3)_3$, triethoxyvinylsilane and 3-glycidoxypropyltrimethoxysilane, and silanes with inorganic radicals which carry hydroxyl, carboxyl, epoxide and carboxylic acid ester groups. The particles modified in such a manner are bonded into the dental material here by incorporation of the particles into the dental material and subsequent polymerization during the actual curing of the dental material.

Preferred metal oxides which are employed for the subsequent coating are $TiO_2$, $Fe_2O_3$ and/or $ZrO_2$.

An embodiment in which filler (A) or (B) is additionally coated with a layer of a polymerizable organic binder based on mono- or polyfunctional (meth)acrylates and/or reaction products of isocyanates and methacrylates containing OH groups is also expedient.

Dental material in the context of the invention is intended to include, inter alia, materials for tooth restoration, such as a tooth filling, inlays or onlays, fixing cements, glass ionomer cements, compomers, veneer materials for crowns and bridges, materials for false teeth, in dentine bondings, underfilling materials, root filling materials or other materials for prosthetic, conservative and preventive dentistry. Composites for dentistry and dental purposes, sealing materials, self-curing composites, stump build-up materials, veneer plastics, dual cements of high and normal filler content and fluoride-containing dental varnishes of normal filler content in particular fall under the term dental material.

Possible binders for the dental material are all those binders based on a polymerizable ethylenically unsaturated monomer with which the person skilled in the art is familiar for this intended use. Polymerizable monomers which can successfully be employed include, preferably, those with acrylic and/or methacrylic groups.

These are in particular, inter alia, esters of α-cyanoacrylic acid, (meth)acrylic acid, urethane(meth)acrylic acid, crotonic acid, cinnamic acid, sorbic acid, maleic acid and itaconic acid with mono- or dihydric alcohols; (meth) acrylamides such as, for example, N-Isobutylacrylamide; vinyl esters of carboxylic acids such as, for example, vinyl acetate; vinyl ethers such as, for example, butyl vinyl ether; mono-N-vinyl compounds such as N-vinylpyrrolidone; and styrene and its derivatives. The mono- and polyfunctional (meth)acrylic acid esters and urethane(meth)acrylic acid esters listed below are particularly preferred.

(a) Monofunctional (meth)acrylates

Methyl (meth)acrylate, n- or i-propyl (meth)acrylate, n-, i- or tert-butyl (meth)acrylate and 2-hydroxyethyl (meth) acrylate.

(b) Difunctional (meth)acrylates

Compounds of the general formula:

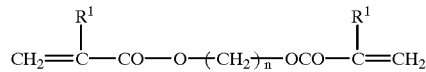

wherein $R^1$ is hydrogen or methyl and n is a positive integer between 3 and 20, such as e. g. the di(meth)acrylate of propanediol, butanediol, hexanediol, octanediol, nonanediol, decanediol and eicosanediol, Compounds of the general formula:

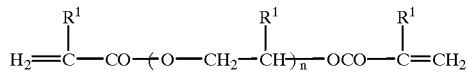

wherein $R^1$ is hydrogen or methyl and n is a positive integer between 1 and 14, such as, for example, the di(meth)acrylate of ethylene glycol, diethylene glycol, triethylene glycol, tetraethylene glycol, dodecaethylene glycol, tetradecaethylene glycol, propylene glycol, dipropylene glycol and tetradecapropylene glycol; and glycerol di(meth)acrylate, 2,2'-bis[p-(γ-methacryloxy-β-hydroxypropoxy)-phenylpropane] or bis-GMA, bisphenol A dimethacrylate, neopentylglycol di(meth)acrylate, 2,2'-di(4-methacryloxypolyethoxyphenyl) propane with 2 to 10 ethoxy groups per molecule and 1,2-bis(3-methacryloxy-2-hydroxypropoxy)butane.

(c) Tri- or Polyfunctional (meth)acrylates

Trimethylolpropane tri(meth)acrylate and pentaerythritol tetra(meth)acrylate.

(d) Urethane(meth)acrylates

Reaction products of 2 mol (meth)acrylate monomer containing hydroxyl groups with one mol diisocyanate and reaction products of a urethane prepolymer containing two NCO end groups with a methacrylic monomer which contains a hydroxyl group, such as are represented e. g. by the general formula:

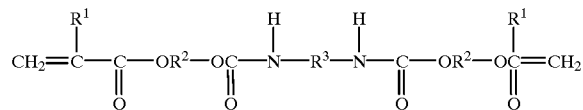

wherein $R^1$ denotes hydrogen or a methyl group, $R^2$ embodies an alkylene group and $R^3$ embodies an organic radical.

Monomers which are especially advantageously employed in the dental material according to the invention include, above all, 2,2-bis-4-(3-methacryloxy-2-hydroxypropoxy)-phenylpropane (bis-GMA), 3,6-dioxaoctamethylene dimethacrylate (TEDMA), and/or 7,7, 9-trimethyl-4,13-dioxo-3,14-dioxa-5,12-diaza-hexadecane-1,16-dioxy-dimethacrylate (UDMA).

A description of the epoxides is given, for example, in DE 961 48 283 A1.

The designation ormocer describes organically modified polysiloxanes such as are listed, for example, in DE 41 33 494 C2 or in DE 44 16 857 and can be used for dental compositions.

Liquid crystal dental monomers are described in EP 0 754 675 A2.

Oxethanes as dental monomers ate described in U.S. Pat. No. 5,750,590 and DE 951 06 222 A1.

Spiro-orthocarbonates are described, for example, in U.S. Pat. No. 5,556,896.

The monomers mentioned may be used either by themselves or in the form of a mixture of several monomers.

The dental material can be polymerized hot, cold and/or by means of light, depending on the nature of the catalyst used. Catalysts which can be employed for the hot polymerization are the known peroxides such as dibenzoyl peroxide, dilauroyl peroxide, tert-butyl peroctoate or tert-butyl perbenzoate, but α,α'-azo-bis(isobutyroethyl ester), benzpinacol and 2,2'-dimethylbenzpinacol are also suitable.

Catalysts which can be used for the photopolymerization are e. g. benzophenone and its derivatives and benzoin and its derivatives. Further preferred photosensitizers are α-diketones such as 9,10-phenanthrenequinone, diacetyl, furil, anisil, 4,4'-dichlorobenziles and 4,4'-dialkoxybenziles, and camphorquinone is particularly preferably used. The use of the photosensitizers together with a reducing agent is preferred. Examples of reducing agents are amines such as cyanoethylmethylaniline, dimethylaminoethyl methacrylate, triethylamine, triethanolamine, N,N-dimethylaniline, N-methyldiphenylamine, N,N-dimethyl-sym.-xylidine and N,N-3,5-tetramethylaniline and ethyl 4-dimethylaminobenzoate.

Systems which supply free radicals, for example benzoyl or lauroyl peroxide, together with amines such as N,N-dimethyl-sym.-xylidine or N,N-dimethyl-p-toluidine, are used as catalysts for the cold polymerization. Dual-curing systems can also be used for the catalysis, for example photoinitiators with amines and peroxides. Mixtures of UV-photocuring catalysts and catalysts which cure in the range of visible light are also possible photocatalysts.

The amount of these catalysts in the dental material is conventionally between 0.01 to 5 wt. %.

The dental material according to the invention is preferably used as a tooth filling material. Tooth filling materials are also prepared as two-component materials which cure in the cold after mixing. The composition is similar to that of photocuring materials, except that instead of the photocatalysts, benzoyl peroxide, for example, is incorporated into the one paste and N,N-dimethyl-p-toluidine, for example, is incorporated into the other paste. A tooth filling material which cures within a few minutes is obtained by mixing approximately equal parts of the two pastes.

If the amine is omitted from the materials mentioned last and, for example, only benzoyl peroxide is used as the catalyst, a heat-curing dental material which can be used for the production of an inlay or of false teeth is obtained. For the production of an inlay, an impression of the cavity is taken in the mouth of the patient and a gypsum model is produced. The paste is introduced into the cavity of the gypsum model and the entire system is polymerized under heat in a pressure pot. The inlay is removed, worked and then cemented into the cavity in the mouth of the patient.

Glass ceramic in the context of the invention is understood as meaning a partly crystalline substance which is built up from amorphous $SiO_2$ compartments in which compartments of crystalline oxides according to the invention are present in embedded form (see also Ullmann's Encyclopedia of Industrial Chemistry $5^{th}$ ed., A12, p.433 et seq.).

The possibility of freely choosing, in the context of the invention, the nature and quantity of the crystalline oxides according to the invention which are incorporated into the amorphous glass composite of filler (A) is consequently the reason why the refractive index of filler (A) can be adjusted to match the refractive index of the surrounding polymer. Only is this way is it ensured that the dental material as a whole is so transparent that it can be cured in one piece in the cavity of the tooth, as required. A troublesome sequential application and curing of the dental material can be omitted. Oxides which are preferably to be employed for this purpose are $TiO_2$, $ZrO_2$, BaO and $WO_3$, and $ZrO_2$ is especially preferably used.

In the same way as for modification of the refractive index, the opacity of filler (A) to X-rays can be adjusted in an ideal manner by embedding crystalline oxide components according to the invention into the amorphous glass matrix. Oxides which are preferably to be employed for this purpose are $TiO_2$, $ZrO_2$, BaO, and $ZrO_2$ is particularly preferably employed.

Possible further fillers (B) are all the fillers with which the person skilled in the art is familiar for improving the quality of the dental material (opacity to X-rays, viscosity, polishability, transparency, strength, refractive index). In order to achieve a further increased opacity to X-rays, it is possible to employ fillers which are described, for example, in DE-OS 35 02 594, but the average primary particle size thereof should not exceed 5.0 μm. Small amounts of microfine pyrogenic silica or silica precipitated in the wet state can optionally be incorporated into the dental material as filler (B).

Possible further fillers (B) are: apatites according to EP 0 832 636 and/or particles according to DE 195 08 586 and/or DE 41 23 946.

The invention also provides a process for the preparation of the dental material according to the invention. This is characterized in that filler (A) is charged with gaseous or liquid polymerizable, ethylenically unsaturated monomers, epoxides, ormocers, liquid crystal monomers, oxethanes, spiro-orthoesters or -carbonates before formulation of the dental material. The abovementioned catalysts are optionally present during the charging, and are then likewise present imbibed in the pores of filler (A).

The charged filler (A) can then be incorporated thus into the organic matrix, or the polymerizable, ethylenically unsaturated monomers present in filler (A) before formulation of the dental material are converted into their polymerized form before the incorporation.

However, the embodiment in which the polymerizable, ethylenically unsaturated monomers present in filler (A) before formulation of the dental material are converted into their polymerized form and the incorporation into the organic matrix is then carried out is preferred.

In addition, filler (A) can additionally be charged with bactericidal agents or chemically modified before the incorporation into the matrix. That stated above on this point applies in this respect.

Charging of filler (A) is thus preferably carried out by treating the micro- and/or mesoporous glass ceramic filler (A) with a vapour of gas and, alternatively, with liquid polymerizable, ethylenically unsaturated monomers described above and optionally the catalysts likewise described above. If the charged filler is now incorporated into the organic matrix, during the subsequent polymerization the monomer in the pores can combine with the monomer outside filler (A) to give a penetrating structure. This operation likewise takes place during the sequential polymerization of the charging material and matrix described above as preferred. By the polymeric network which is constructed in filler (A) and is bonded chemically on the exo-side with the binder of the dental material it is ensured that a certainly strong physical bond is formed between filler (A) and the binder of the dental material, and this can no longer be destroyed by hydrolysis. A dental material which is distinguished by a particular abrasion resistance coupled with a simultaneously high flexural strength which is not achieved by comparable dental materials of the prior art is thus obtained. The cleavage between the organic particles and the organic matrix is also thereby almost entirely suppressed. This increases the storage stability of the dental compositions according to the invention, since hydrolytic cleavage of the bond between organic and inorganic constituents which starts in the course of time, as is known of the materials of the prior art, can no longer occur.

Another aspect of the invention is concerned with porous glass ceramics which are charged with polymerizable, ethylenically unsaturated monomers or with the polymerized form thereof. By providing these, it is possible to provide fillers for dental materials which are superior to the materials of the prior art in an inexpensive process. Porous glass ceramics which have a pore size of >1 nm and <1000 nm, the particle size of which is between 10 and 30 μm and which have a pore volume of >500 $mm^3/g$ and <1500 $mm^3/g$, are preferably employed for this purpose. The crystalline content of the glass ceramic preferably comprises oxides of metals of main groups 1–4 and/or oxides of metals of the sub-groups. These oxides are contained in the glass ceramic up to a content of 1–50 wt. %, based on the glass ceramic. That stated for filler (A) otherwise applies in respect of the glass ceramic.

In another aspect, the invention relates to a porous glass ceramic, the pore volume of which is between 500 $mm^3/g$ and 1500 $mm^3/g$. According to the invention, this preferably has a pore size of >1 nm and <1000 nm. The particle size of the ceramic can preferably be between 10 and 30 μm. In addition to its amorphous $SiO_2$ content, it is built up from crystalline regions which comprise oxides of metals of main groups 1–4 and oxides of metals of the sub-groups. The content of these oxides in the glass ceramic body is between 1 and 50 wt. %. That stated for the charged glass ceramic otherwise applies in respect of the porous glass ceramic.

Another aspect of the invention relates to a process according to the invention for the preparation of the glass ceramics, in which the glass ceramic is prepared by mixing an aqueous $SiO_2$ sol and one or more aqueous sols of oxides of metals of main groups 1 to 4 and of oxides of metals of the sub-groups.

0–20 wt. %, based on the sol mixture, of an aqueous solution of a salt can preferably additionally be added to the sol mixture. Salts which can be used are in principle all the metal salts considered suitable for this purpose by the person skilled in the art. Metal salts such as alkali metal nitrates and/or acetates and nitrates of metals of the sub-groups are preferably to be employed. The addition of solutions of metal salts to the sol mixture allows the preparation of powders of high strength. However, salts also influence the surface chemistry of the resulting powders, which is of decisive importance for many intended uses (catalysts). They moreover determine the properties of the powders during the subsequent heat treatment to a large extent. It is thus possible, for example, to build up particles which have a chemical gradient in composition from the inside to the outside, so that ceramic powder grains in which the shell and core have different chemical and physical properties are formed.

0–10 wt. % (based on the mixture) of organic solvents can likewise optionally be added to the sol mixture. Short-chain alcohols, short-chain acids and chelating solvents such as acetyl acetonate may be mentioned as organic solvents which are preferably to be employed.

The sol mixture is then dried in a stream of gas. The sol mixture is preferably spray-dried. In principle, however, other drying procedures known to the person skilled in the art, such as, for example, lyophilization, can also be used for preparation of the glass ceramic.

Finally, the spray-dried sol mixture is calcined at >800° C. and <1300° C.

The charged or non-charged porous glass ceramic is preferably employed in dental materials.

The preparation of ceramic powders with the abovementioned properties requires the use of various precursors, each of which has a dominant influence on a main feature of the resulting powder.

Precursors which are chosen are an oxide of silicon, at least one further oxide of metals of main groups 1 to 4 or of sub-group metals and possibly a salt.

Suitable silicon oxides are, for example, powders prepared by the pyrolytic route. They are suspended in an aqueous solvent, so that a sol is formed. With suitable choice of the starting sols, granules in which the ratio of the pore widths $d_{10}$ and $d_{90}$ does not exceed the number 2.5 are formed. $d_{10}$ here designates the pore width which the content of 10 vol. % of the largest pores does not exceed, and $d_{90}$ designates the pore width which the content of 90 vol. % of the largest pores does not fall below.

All oxides which can be prepared as a suspension of non-agglomerated, nanoscale particles can be used as oxides which are responsible for establishing the physical and chemical properties. Sols which are formed by hydrolysis and condensation reactions of metal salts and alcoholates are suitable above all here.

Solutions of metal salts can be added as a third component. They allow the preparation of glass ceramics of high strength.

The ceramic powders are prepared by mixing the aqueous sol of an oxide of silicon which has primary particles agglomerated in a defined manner and contains no or only a small content of organic additives with the sol or sols of other oxides and the salt solutions and then solidifying the mixture in a hot stream of gas by removal of the solvent. The spray drying process is suitable for this. Agglomerate-free ceramic powders with spherical grains, adjustable pore volumes and high strength can be prepared with the aid of a subsequent heat treatment.

The dental materials according to the invention described herein can be prepared in an economically acceptable manner because of the glass ceramic fillers (A) which are inexpensive to prepare and nevertheless no less advantageous.

By the discovery of the new porous glass ceramics or fillers (A) as components in new dental materials, acceptable (in respect of workability, fashion acceptance, strength, abrasion resistance, polymer shrinkage, storage stability, price etc.) alternatives to the amalgams which are still mostly employed in the chewing region are consequently obtained.

DETAILED DESCRIPTION OF THE INVENTION

The following examples are intended to illustrate the invention.

EXAMPLE 1

AEROSIL® 200 (Degussa AG) is incorporated into water with the aid of an Ultraturrax such that a suspension is formed. This sol is agitated on a shaking machine for 2 days. The $SiO_2$ sol is then mixed with the sols mentioned below, so that the weight ratios of the solids mentioned in the table result.

A zirconium oxide sol is prepared by heating an acetic acid solution of zirconium acetate until gelling occurs. By suitable choice of the pH and lowering in temperature, the gel can be peptized again, so that a sol with isolated $ZrO_2$ particles, the diameters of which are less than 30 nm, is formed. The sol is transparent. The pH must be adjusted such that no spontaneous gelling occurs on mixing with the $SiO_2$ sol.

A titanium oxide sol is prepared by heating a basic aqueous solution of titanium(IV) bis-(ammonium lactate) dihydroxide until the first opalescence occurs. The sol also remains largely transparent during storage. The pH must be adjusted such that no spontaneous gelling occurs on mixing with the $SiO_2$ sol.

Powders with the compositions mentioned below can be prepared by spray drying of the sol mixtures and subsequent calcining. Powders which have been prepared exclusively with the aid of the $SiO_2$ sol are included for comparison.

Spray drying is carried out at temperatures below 200° C. at a constant flow rate.

| Weight content $ZrO_2$ | Weight content $SiO_2$ | Refractive index $n_D$ | Density (g/cm$^3$) |
|---|---|---|---|
| 0 | 100 | 1.472 (2) | 2.26 (1) |
| 10 | 90 | 1.509 (2) | 2.39 (1) |
| 30 | 70 | 1.59 (1) | 2.70 (1) |
| 50 | 50 | 1.68 (1) | 3.23 (1) |

EXAMPLE 2

The preparation of the powders mentioned below largely corresponds to that mentioned in example 1, but on the one hand AEROSIL® 200 (Degussa AG) and on the other hand AEROSIL® 90 (Degussa AG) is used to prepare the $Sio_2$ sol. The pore widths, which are determined by the AEROSIL® used, are also retained on addition of $ZrO_2$.

| Weight content $ZrO_2$ | Weight content $SiO_2$ | AEROSIL® type | Calcining temperature (° C.) | Pore width (nm) |
|---|---|---|---|---|
| 0 | 100 | AEROSIL® 90 | 1100 | 62 (2) |
| 10 | 90 | AEROSIL® 90 | 1100 | 60 (2) |
| 0 | 100 | AEROSIL® 200 | 1050 | 32 (2) |
| 10 | 90 | AEROSIL® 200 | 1050 | 32 (2) |

EXAMPLE 3

By varying the calcining temperature or the calcining time, the pore volume can be varied over a wide range, with the pore widths largely constant, as can be seen for a power with 10 wt. % $ZrO_2$ from the table below by way of example. Varying the calcining time leads to a similar behaviour.

| Calcining temperature (° C.) | Calcining time (h) | Pore volume ($mm^3$/g) | Pore width (nm) | Spec. surface area [$m^2$/g] |
|---|---|---|---|---|
| 900 | 5 | n.d. | 35 (2) | n.d. |
| 1000 | 5 | 1279 (64) | 33 (2) | 125 |
| 1050 | 5 | 881 (44) | 32 (2) | 115 |
| 1100 | 5 | 287 (15) | 25 (2) | 52 |

EXAMPLE 4

By using metal salts in addition to the starting substances mentioned in example 2, for example, the calcining can be controlled. The table below gives an example of the pore characteristics such as are to be observed for a glass ceramic with 10% $ZrO_2$ and 90% $SiO_2$ with addition of sodium nitrate.

| Addition of sodium nitrate | Calcining temperature (° C.) | Calcining time (h) | Pore volume ($mm^3$/g) | Pore width (nm) | Spec. surface area [$m^2$/g] |
|---|---|---|---|---|---|
| no | 900 | 5 | n.d. | 35 (2) | n.d. |
| no | 1000 | 5 | 1279 (64) | 33 (2) | 125 |
| yes | 900 | 5 | n.d. | 31 (2) | n.d. |
| yes | 1000 | 5 | 172 | 20 (2) | 40 |

The porous fillers described are further processed to dental filling materials. For this, they are mixed with further components, as described in example 5. The flexural strength and the E modulus are determined in the 3-point bending test. Details on the specimen geometry and the test method are to be found in the standard ISO 4049:1988.

EXAMPLE 5

52.87 g of the silanized porous filler from example 2, together with 0.034 wt. % camphorquinone are incorporated, under a vacuum of 200 mbar, into 47.13 g of a monomer mixture comprising 35 parts bis-GMA, 35 parts UDMA and 30 parts TEGDMA. The paste formed is cured by means of light (Degulux®). Flexural strength: 92±6 MPa, E modulus: 4765±89 Mpa.

Dental material comparison example:

The comparison with the prior art relates to the product Solitaire from Kulzer. This material comprises approx. 30 wt. % of a porous filler comprising 100 % $SiO_2$ and additionally for reinforcement also approx. 30 wt. % compact glass particles of average particle size 0.7 μm. The strength properties were measured in the manner described above. Flexural strength: 51±6 MPa, E modulus: 2765±89 MPa.

References and patents cited herein are hereby incorporated by reference.

What is claimed is:

1. A dental composition comprising:
   a) a polymerizable compound selected from the group consisting of: ethylenically unsaturated monomers; epoxides; ormocers; liquid crystal monomers; oxetanes; spiro-orthoesters; and spiro-carbonates;
   b) a catalyst for cold, hot or photo-polymerization; and
   c) an inorganic filler in the form of a ceramic glass impregnated with said polymerizable compound wherein;
      i) said inorganic filler is present at a concentration of 20–70 wt. %;
      ii) in addition to said ceramic glass, said inorganic filler comprises a crystalline oxide at a concentration such that, upon polymerization of said dental composition, the refractive index of said filler matches the refractive index of the surrounding polymer; and
      iii) said inorganic filler has a pore volume of between 200 and 2,000 $mm^3$/g.

2. The dental composition of claim 1, wherein said crystalline oxide comprises a metal of main groups I–IV of the periodic table or of a subgroup.

3. The dental composition of claim 1, wherein said crystalline oxide is selected from the group consisting of: $TiO_2$; $ZrO_2$; BaO; $WO_3$; and $FeO_2$.

4. The dental composition of any one of claims 1–3, wherein said inorganic filler has a pore size greater than 10 nm and less than 100 nm.

5. The dental composition of any one of claims 1–3, wherein said inorganic filler has a particle size of between 10 and 30 μm.

6. The dental composition of any one of claims 1–3, wherein said inorganic filler has a pore volume greater than 500 $mm^3$/g and less than 1500 $mm^3$/g.

7. The dental composition of any one of claims 1–3, wherein said dental composition further comprises at least one additional filler present at 5–20 wt. %; and wherein said polymer is present at 30–50 wt. % and said inorganic filler is present at 30–60 wt. %.

8. The dental composition of any one of claims 1–3, further comprising a bactericidal agent.

9. The dental composition of any one of claims 1–3, wherein the surface of said inorganic filler is chemically modified.

* * * * *